(12) United States Patent
Clare et al.

(10) Patent No.: US 6,391,291 B1
(45) Date of Patent: May 21, 2002

(54) ANTIPERSPIRANT COMPOSITIONS

(75) Inventors: Sarah Jayne Clare; Kevin Ronald Franklin; Angela Mary Murphy; Kathryn Elizabeth Gransden (nee Rowe); Graham Andrew Turner, all of Merseyside (GB)

(73) Assignee: Unilever Home & Personal Care, USA division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/902,276

(22) Filed: Jul. 10, 2001

(30) Foreign Application Priority Data

Jul. 10, 2000 (GB) .............................................. 0016937

(51) Int. Cl.$^7$ ............................ A61K 7/32; A61K 7/34; A61K 7/38; A61K 7/00; A61K 31/74
(52) U.S. Cl. ............................ 424/65; 424/66; 424/68; 424/78.02; 424/78.08; 424/400; 424/401
(58) Field of Search .............................. 424/65, 66, 68, 424/78.02, 78.08, 400, 401

(56) References Cited

U.S. PATENT DOCUMENTS

| 4,265,878 A | 5/1981 | Keil ............................ 424/68 |
| 4,704,271 A | 11/1987 | Hourihan et al. .............. 424/66 |
| 4,719,102 A | 1/1988 | Randhawa et al. ............ 424/66 |
| 4,719,103 A | 1/1988 | Krevald et al. ................ 424/66 |
| 4,725,430 A | 2/1988 | Schamper et al. ............. 424/66 |
| 4,725,431 A | 2/1988 | Hourihan et al. .............. 424/66 |
| 4,732,754 A | 3/1988 | Krevald ........................ 424/66 |
| 4,822,602 A | 4/1989 | Sabatelli ...................... 424/65 |
| 5,200,174 A | 4/1993 | Gardlik et al. ................. 424/66 |
| 5,346,694 A | 9/1994 | Juneja .......................... 424/66 |
| 5,429,816 A | 7/1995 | Hofrichter et al. ............ 424/66 |
| 5,455,026 A | 10/1995 | Bahr et al. ..................... 424/65 |
| 5,480,286 A | 1/1996 | Gardlik ........................ 424/65 |
| 5,480,637 A | 1/1996 | Smith ...................... 424/78.02 |
| 5,492,691 A | 2/1996 | Bahr et al. ..................... 404/65 |
| 5,500,209 A | 3/1996 | Ross et al. ..................... 424/66 |
| 5,635,165 A | 6/1997 | Panitch ........................ 424/65 |

FOREIGN PATENT DOCUMENTS

| EP | 616 842 | 9/1994 |
| WO | 97/13496 | 4/1997 |
| WO | 97/36572 | 10/1997 |
| WO | 97/36573 | 10/1997 |
| WO | 99/06473 | 2/1999 |

*Primary Examiner*—Shelley A. Dodson
(74) *Attorney, Agent, or Firm*—Kevin J. Stein

(57) ABSTRACT

A firm solid antiperspirant composition having a continuous phase comprising water-immiscible liquid containing i) one or more gelating structurant materials which form a network of fibres within the liquid, and ii) a polymeric thickener which has an organic polymer backbone containing at least five monomer repeat units, which polymer has the ability to increase the viscosity of the water-immiscible liquid in the absence of the gelating structurant materials; and iii) an antiperspirant active dispersed in the continuous phase, said composition being free from or containing less than 3% by weight of a fatty alcohol that is solid at 20° C.

23 Claims, No Drawings

ANTIPERSPIRANT COMPOSITIONS

FIELD OF THE INVENTION

The present invention relates to antiperspirant compositions with sufficient rigidity to sustain their own shape. The usual form of such compositions is a stick.

BACKGROUND OF THE INVENTION

Topically applied antiperspirant compositions are in widespread use throughout much of the world, in order to enable their users to avoid or minimise wet patches on their skin, especially in axillary regions. Antiperspirant formulations have been applied using a range of different applicators depending on the individual preferences of consumers, including aerosols, roll-ons, pump sprays, sticks and so-called mushroom applicators which are used to apply cream formulations. In some parts of the world, sticks are especially popular. The term stick traditionally indicates a bar of material with a solid appearance which is usually housed within a dispensing container and which retains its structural integrity and shape whilst being applied. When a portion of the stick is drawn across the skin surface a film of the stick composition is transferred to the skin surface. Although the stick has the appearance of a solid article capable of retaining its own shape for a period of time, the material usually has a structured liquid phase so that a film of the composition is readily transferred from the stick to another surface upon contact.

For use, the stick is applied directly to the skin of the user. This contrasts with soft solid compositions which exist as a stick within their container but for use a portion is extruded from the container through apertures which have smaller cross section than the body of composition which is being made to flow out through these apertures.

Antiperspirant sticks have been made with a variety of different types of composition. Suspension sticks contain a particulate antiperspirant active suspended in a structured carrier material which is generally water-immiscible and may well be anhydrous. Solution sticks have the antiperspirant active dissolved in a structured carrier which is polar and may be aqueous or may be based on a non-aqueous polar solvent such as ethanol. A third form of stick is an emulsion of two phases where the continuous phase is structured so that the composition is able to sustain its own shape, the antiperspirant active being dissolved in the more polar of the two phases present. In some emulsion sticks the antiperspirant active is dissolved in an aqueous disperse phase while the continuous phase is a liquid water-immiscible phase so that the composition can be classified as a water-in-oil emulsion. The classification into suspension, emulsion and solution types can be applied to both firm and soft solid compositions.

There is substantial literature on the structuring or thickening of antiperspirant compositions which is frequently accomplished using some form of thickening agent as part of the composition.

It has been common practice for sticks to be structured by incorporating fatty alcohol into the composition, often accompanied by a smaller amount of castor wax. Sticks which are structured with fatty alcohol tend to leave visible white deposits on application to human skin. These deposits can also transfer onto clothing when it comes into contact with the skin and the wearer can, for example, find white marks on the armhole of a sleeveless garment. Fatty alcohols are often regarded as coming within the general category of waxy materials, but we have observed that they are a more significant source of white deposits than other waxy materials.

There have been some disclosures of antiperspirant stick compositions where structuring to a shape-sustaining stick has been accomplished without using a fatty alcohol. Amongst these disclosures there has sometimes been recognition that white deposits are avoided.

The thickening of organic liquids with polyamides in order to make antiperspirant compositions has been disclosed in U.S. Pat. No. 5500209. Typically, compositions exemplified in this document are thickened with 15% or more of thickening polymer, and are emulsions in which the antiperspirant active is dissolved in water or hydrophilic solvent.

WO 97/36572 WO 97/36573 and WO 99/06473 all disclose the structuring of antiperspirant sticks with siloxane polymers which incorporate amide and/or other hydrogen bonding substituent groups.

We have found that when emulsion sticks are structured solely with such polymer according to these prior documents, the result is unsatisfactory. Over 10% polymer was required to obtain firm sticks, but these were then found to have a rubbery, tacky feel. Moreover pieces could be broken off easily.

WO 97/13496 employs polyethyleneformamides to form an antiperspirant gel in an aqueous or water-miscible medium. It provides no teaching of relevance to structuring a water-immiscible liquid carrier.

U.S. Pat. No. 4,265,878, U.S. Pat. No. 4,725,431, U.S. Pat. No. 4,732,754, U.S. Pat. No. 4,719,103 and U.S. Pat. No. 4,704,271 disclose antiperspirant stick compositions in which a solution of antiperspirant active in aqueous solution is dispersed in a hydrophobic continuous phase of hydrocarbon or silicone oil. This hydrophobic continuous phase is structured to provide a rigid stick by the incorporation of a substantial amount of waxy material, such as stearyl alcohol or spermaceti wax.

U.S. Pat. No. 4,822,602 exemplifies a composition structured with sodium stearate which restricts the choice of antiperspirant active to an unusual active which does not precipitate as an insoluble salt on contact with stearate, but is of poor efficacy. The sodium stearate causes phase transfer of a water-miscible constituent. A stick prepared in accordance with this example was found to have a tacky, draggy feel on handling.

In some cases structuring has been achieved by the incorporation of a structurant (also referred to as a gellant or gelling agent) which causes the liquid to gel upon cooling from an elevated temperature. Gel formation takes place as an exothermic event within a temperature range referred to as the gel point; upon reheating, melting of the gel takes place as an endothermic event within a temperature range. Such gels can be disrupted by shearing and do not recover their structure for a long time, if at all unless remelted, although a small partial recovery may be observed.

U.S. Pat. No. 5,429,816 discloses an antiperspirant stick in which a solid antiperspirant active is dispersed in a carrier mixture of silicone and other oil which is gelled with 12-hydroxy stearic acid used jointly with a secondary gellant which is an n-acyl-amino acid amide. The deposit on skin is said to be a low visible residue, rather than an opaque white deposit. A number of other documents provide similar disclosures of suspension sticks structured with these materials.

U.S. Pat. No. 5,480,637 discloses the preparation of an antiperspirant stick in which a suspension of solid, encapsulated aluminium chlorohydrate dispersed in silicone oil is gelled with 12-hydroxy stearic acid used jointly with a small amount of an alkyl methyl siloxane polymer. U.S. Pat. No. 5,492,691, U.S. Pat. No. 5,455,026 and EP-A-616842 are somewhat similar but do not require the siloxane polymer. Although U.S. Pat. No. 5,480,637 teaches the use of siloxane polymer to promote the gelling action of 12-hydroxystearic acid, we have found that it has very little effect.

U.S. Pat. No. 5,840,286 is concerned with anhydrous suspension sticks containing a gelling agent and requires that the composition is substantially free of organic polymeric gellant.

U.S. Pat. No. 4,719,102, U.S. Pat. No. 4,725,430, U.S. Pat. No. 5,200,174 and U.S. Pat. No. 5,346,694 all disclose sticks formed by mixing two solutions both of which contain a substantial amount of a polar solvent. One contains dibenzylidene sorbitol or a similar compound as a structurant while the other contains the antiperspirant active dissolved in an alcohol solution with little water present. The alcoholic solution generally contains ethanol or a mixture of ethanol and propylene glycol. The two solutions become one by mixing, and can incorporate a water-soluble polymer. Formulating a stick to contain substantial amounts of polar organic solvent has associated disadvantages. If the polar solvent is volatile, like ethanol, the stick gives a cooling sensation when applied. Some cooling may be desired but too much may prove unacceptable to consumers. Polar but less volatile solvents such as water-immiscible diols tend to make a stick feel tacky when touched and hence give a sensation of stickiness and drag when applied to skin.

Fatty acyl amino acid amides, 12-hydroxy stearic acid and dibenzylidene sorbitol are all examples of compounds which are able to gel and hence structure at least some organic liquids, (although dibenzylidene sorbitol is not suitable if an acidic aqueous phase is present, because it will be hydrolysed rapidly). It has been shown that they function by forming a network of fibres which extend throughout the liquid and thereby give it rigidity. When the gel melts these fibres dissolve in the liquid.

WO 99/66895 discloses stick shaped cosmetic formulations containing essentially a linear aliphatic alcohol such as stearyl alcohol and 12-hydroxystearic acid. Optionally an organic thickener can be incorporated. Such formulations inevitably have impaired visual deposition because of the incorporation of the linear aliphatic alcohol.

SUMMARY OF THE INVENTION

We have now found that a good combination of properties can be achieved by gelation with a gel-forming structurant and supplementing this with a polymeric thickener which is organic rather than a silicone polymer.

According to a first aspect of this invention there is provided a firm solid antiperspirant composition having a continuous phase comprising water-immiscible liquid containing:
i) one or more gelating structurant materials which form a network of fibres within the liquid, and
ii) a polymeric thickener which has an organic polymer chain containing at least five monomer repeat units and providing a polymeric main chain consisting of carbon atoms optionally together with oxygen or nitrogen, which polymer has the ability to increase the viscosity of the water-immiscible liquid in the absence of the gelating structurant materials; and
iii) an antiperspirant active dispersed in the continuous phase which composition is free from or contains less than 3% by weight of a fatty alcohol which is solid at 20° C.

A composition of this invention may be a suspension of particulate antiperspirant active, or an emulsion in which the disperse liquid phase is a solution of antiperspirant active in water or other hydrophobic solvent.

In either case, a composition of this invention is a firm solid which is able to sustain its own shape if left unsupported.

The gelating structurant material may be a single such material, a mixture of such materials or a plurality of materials which co-operate to form a gelating system. The total amount of such structuring materials is preferably sufficient to gel the water-immiscible liquid, in absence of the polymeric thickener, to a state which is able to sustain its own shape at 20° C. at least for a time.

The polymeric thickener must have an organic backbone, i.e. main chain, containing carbon atoms, and possibly other atoms such as oxygen and nitrogen. Silicon atoms should be substantially absent from the backbone chain. The presence of silicon atoms in side chains or in terminal or substituent groups is not ruled out although preferred polymers do not contain any silicon, and so can be classed as silicon-free organic polymers. These structural requirements distinguish from siloxanes which have a polymeric chain of silicon and oxygen atoms, with carbon atoms in substituent and terminal groups.

Preferred organic polymers for this invention are polysaccharides esterified with fatty acyl groups containing at least eight carbon atoms. The amount of organic polymer is preferably such that, in the absence of the gelating structurant materials, it will thicken the water immiscible liquid to a viscous, yet still mobile state which is incapable of sustaining its own shape, with a consequence that if disturbed it will be seen to flow to restore a level surface.

Alternative organic polymer thickening agents comprise block copolymers of styrene with an alkylene containing up to 5 carbons.

Compositions of the present invention can provide:
satisfactory hardness of the composition,
satisfactory sensory perception when applied to the skin by the user
avoidance of highly visible opaque deposits on skin or clothing
Incorporation of the polymer as a supplement to the gelating structurant can provide one or more of:
an increase in hardness of the composition
an increase in stability of the composition, notably a reduction in syneresis, that is to say liquid weeping from the body of composition
improved efficacy.

In order to promote good sensory properties at the time of use it is preferred to include silicone oil in the water-immiscible carrier liquid. The amount of silicone oil may be at least 10% by weight of the composition and/or at least 40% by weight of the water-immiscible carrier liquid.

Ethanol gives a cooling effect on application to skin, because it is very volatile. It is preferred that the content of ethanol or any monohydric alcohol with a vapour pressure above 1.3 kPa (10 mm Hg) is not over 15% better not over 8% by weight of the composition.

Fatty alcohols which are solid at room temperature of 20° C., such as stearyl alcohol, lead to deposits with an opaque white appearance and are kept to low concentration, preferably not more than 2% by weight or entirely excluded. Such fatty alcohols are commonly linear aliphatic alcohols containing at least 12 carbons, of which stearyl alcohol is the example of such linear alcohols most commonly encountered in antiperspirant compositions. As already mentioned, fatty alcohols are often regarded as coming within the general category of waxy materials. More generally the term "wax" is conventionally applied to a variety of materials and mixtures (including some fatty alcohols) which have some diversity in chemical structure but similarity in physical properties. The term generally denotes materials which are solid at 30° C., often also solid up to 40° C., but which melt to a mobile liquid at a temperature below 95° C. usually below 90° C.

Preferably the composition does not include more than 3% of any material which is solid at 30° C. but is molten at 95° C. and at 95° C. is soluble in the water-immiscible liquid of the continuous phase, and which is unable to form a network of fibres in the continuous phase on cooling to 20° C.

A composition of this invention will generally be marketed in a container by means of which it can be applied at time of use. This container may be of conventional type.

A second aspect of the invention therefore provides an antiperspirant product comprising a dispensing container having an open end for delivery of the contents of the container, means for urging the contents of the container to the said open end, and a stick of composition of the first aspect of the invention in the container.

The compositions of this invention can be made and packed by heating their constituents to form a liquid composition, mixing at temperatures where the composition is freely mobile, pouring into containers for retail sale and leaving these compositions to cool to room temperature. The composition thickens and solidifies as it cools. Therefore, in a third aspect, this invention provides a method of making a composition as specified above, by steps of mixing the ingredients of the composition, and before, during or after mixing, heating the ingredients of the composition to a temperature at which the continuous phase is a mobile liquid in which the gelating structurant material (i) and the polymeric thickener (ii) are dissolved in the water-immiscible liquid, followed by:
introducing the mixture into a mould which preferably is a dispensing container, and then
cooling or permitting the mixture to cool to a temperature at which it is solidified, suitably a temperature below 30° C.

In many instances, the method will commence with mixing the ingredients of the continuous phase and before, during or after this mixing heating these constituents to a temperature at which the continuous phase is a mobile liquid in which the gelating structurant material (i) and the polymeric thickener (ii) are dissolved in the water-immiscible liquid, followed by mixing a disperse phase comprising antiperspirant active into the continuous phase, and thereafter introducing the resulting mixture into a mould and cooling or allowing cooling.

As already indicated the disperse phase may be antiperspirant active in particulate form, or may be solution of antiperspirant active in a polar, possibly aqueous, solvent.

According to a fourth aspect of the present invention, there is provided a method for preventing or reducing perspiration on human skin comprising topically applying to the skin a composition according to the first aspect of this invention comprising an antiperspirant active, a water-immiscible liquid carrier and a structurant therefor.

DETAILED DESCRIPTION AND EMBODIMENTS

As mentioned above, the invention requires both an organic polymeric thickener and another structurant within a water-immiscible liquid phase. Other materials may also be present depending on the nature of the composition. The various materials will now be discussed by turn and preferred features and possibilities will be indicated.

Water-immiscible Liquid

The water-immiscible liquid comprise one or a mixture of materials which are relatively hydrophobic so as to be immiscible in water. Some hydrophilic liquid may be included, provided the overall liquid mixture is immiscible with water. Generally, this liquid or liquid mixture (when in the absence of polymeric thickener or other structurant) will be freely mobile at temperatures of 15° C. and above. It may have some volatility, but its vapour pressure will generally be less than 4 kPa (30 mmHg) at 25° C. so that the material can be referred to as an oil or mixture of oils. More specifically, it is desirable that at least 80% by weight of the liquid should consist of materials with a vapour pressure not over this value of 4 kPa at 25° C.

It is preferred that the liquid or liquid mixture includes a volatile liquid silicone, i.e. liquid polyorganosiloxane. To class as "volatile" such material should have a measurable vapour pressure at 20 or 25° C. Typically the vapour pressure of a volatile silicone lies in a range from 1 or 10 Pa to 2 kPa at 25° C.

It is desirable to include volatile silicone because it gives a "drier" feel to the applied film after the composition is applied to skin.

Volatile polyorganosiloxanes can be linear or cyclic or mixtures thereof. Preferred cyclic siloxanes include polydimethylsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $10^{-5}$ m$^2$/sec (10 centistokes), and particularly above $10^{-7}$ m$^2$/sec (0.1 centistokes), the linear siloxanes normally exhibiting a viscosity of below $5 \times 10^{-6}$ m$^2$/sec (5 centistokes). The volatile silicones can also comprise branched linear or cyclic siloxanes such as the aforementioned linear or cyclic siloxanes substituted by one or more pendant -0-Si(CH$_3$)$_3$ groups. Examples of commercially available silicone oils include oils having grade designations 344, 345, 244, 245 and 246 from Dow Corning Corporation; Silicone 7207 and Silicone 7158 from Union Carbide Corporation; and SF1202 from General Electric.

The hydrophobic liquid employed in compositions herein can alternatively or additionally comprise non-volatile silicone oils, which include polyalkyl siloxanes, polyalkylaryl siloxanes and polyethersiloxane copolymers. These can suitably be selected from dimethicone and dimethicone copolyols. Commercially available non-volatile silicone oils include Dow Corning 556 and Dow Corning 200 series.

The water-immiscible liquid may contain from 0 to 100% by weight of one or more liquid silicones. Preferably, there is sufficient liquid silicone to provide at least 10%, better at least 15%, by weight of the whole composition. If silicone oil is used, volatile silicone preferably constitutes from 20 to 100% of the weight of the liquid or liquid mixture. In many instances, when a non-volatile silicone oil is present, its weight ratio to volatile silicone oil is chosen in the range of from 1:3 to 1:40.

Silicon-free hydrophobic liquids can be used instead of, or more preferably in addition to liquid silicones. Silicon-free hydrophobic organic liquids which can be incorporated include liquid aliphatic hydrocarbons such as mineral oils or hydrogenated polyisobutene, often selected to exhibit a low viscosity. Further examples of liquid hydrocarbons are polydecene and paraffins and isoparaffins of at least 10 carbon atoms. Although polyisobutene and polydecene are polymeric in nature, they are mobile liquids at room temperature of 20° C. and do not cause thickening of other hydrophobic oils.

Some hydrophobic aliphatic or aromatic esters are liquids which may be used. These also may be used as only part of a liquid mixture.

Suitable aliphatic esters contain at least one long chain alkyl group, such as esters derived from $C_1$ to $C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they each have a melting point of below 20° C. These esters include isopropyl myristate, lauryl myristate, isopropyl palmitate, diisopropyl sebacate and diisopropyl adipate.

Suitable liquid aromatic esters, preferably having a melting point of below 20° C., include fatty alkyl benzoates. Examples of such esters include suitable $C_8$ to $C_{18}$ alkyl benzoates or mixtures thereof.

As mentioned above, aliphatic alcohols which are solid at 20° C., such as stearyl alcohol are preferably absent or else present in low concentration such as less than 5% by weight of the whole composition since these lead to visible white deposits when a composition is used.

However, aliphatic alcohols which are liquid at 20° C. may be employed. These include branched chain alcohols of at least 10 carbon atoms such as isostearyl alcohol and octyl dodecanol.

Silicon-free liquids can constitute from 0–100% of the water-immiscible liquid, but it is preferred that silicone oil is present and that the amount of silicon-free liquid constituents preferably constitutes no more than 50 or 60% and in many instances from 20 to 60% by weight of the liquid mixture.

Organic Polymeric Thickener

A number of organic polymers are effective to increase the viscosity of hydrophobic liquids, although some polymers do not do so.

A material which is suitable as an organic polymeric thickener will generally possess the following characteristics:

i) it will contain residues of at least 5 possibly many more than 7) monomer units bonded together into a polymer chain;

ii) it should dissolve sufficiently on heating in hydrophobic oils, more specifically in the water-immiscible liquid of the continuous phase;

iii) after heating to dissolve and cooling to 20° C., it will increase the viscosity of the water-immiscible liquid of the continuous phase in the absence of other structurant: this should be observable with the polymer dissolved at a concentration not exceeding 6% by weight.

Preferably, under these conditions, it will bring about a viscosity increase of at least 100 mpa.sec, better at least 250 mpa.sec when viscosity is measured with a Brookfield viscometer using a T-bar spindle at 10 rpm at 20° C. The choice of a type B, type C or type D T-bar spindle will depend on the viscosity of the system being measured. Provided the spindle is appropriate to provide a viscosity measurement it will enable determination of an increase in viscosity brought about by the polymer.

An additional or alternative characterisation of a suitable polymer is that it can thicken the water-immiscible liquid to a viscosity of at least 10,000 mpa.sec, measured in the same way, when incorporated in the water-immiscible liquid at not more than 6% by weight, in the absence of the other structurant.

The polymer will generally be solid at 20° C.

One category of polymer which has been found suitable is a polysaccharide esterified with a monocarboxylic acid containing at least 8 carbon atoms.

Preferred in this category is a dextrin fatty acid ester having the formula:

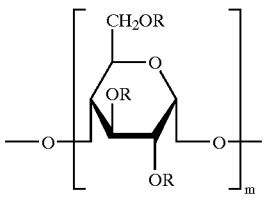

wherein each R group, individually, is a hydrogen or an acyl group of up to 22 carbon atoms, provided that at least one R group per glucose unit is an acyl group of 8 to 22 carbon atoms, and m has a value from about 20 to 30. The dextrin fatty acid ester can be a partial ester, i.e. at least one R group is hydrogen. Another possibility is that the dextrin can be completely esterified with $C_8$ to $C_{22}$ acyl groups, i.e. every R group is a $C_8$–$C_{22}$ acyl group. In preferred embodiments, the degree of substitution with an R group which is a $C_8$–$C_{22}$ alkyl group is at least 2 (i.e., at least two R groups are $C_8$–$C_{22}$ acyl groups). A further possibility would be that some R groups are acyl groups of less than 8 carbon atoms while some R groups (at least one per glucose residue, preferably at least two) is a $C_8$ to $C_{22}$ acyl group. The $C_8$–$C_{22}$ fatty acids that provide acyl groups can be saturated or unsaturated acids, and include, for example, capric acid, pelargonic acid, caprylic acid, undecylic acid, undecylenic acid, lauric acid, myristic acid, pentadecylic acid, palmitic acid, heptadecylic acid, stearic acid, nonadecanoic acid, arachic acid, oleic acid, linoleic acid, linolenic acid, similar acids, and mixtures thereof. Dextrin fatty acid esters are disclosed in Mori et al U.S. Pat. No. 4,780,145, incorporated herein by reference, and some of them are available under the trade name RHEOPEARL from Chiba Flour Milling Co., Ltd., Japan. An example of a dextrin fatty acid ester is dextrin palmitate, available commercially as RHEOPEARL KL and RHEOPEARL FL, for example, from Chiba Flour Milling Co., Ltd. Other examples of esters of $C_8$–$C_{22}$ carboxylic acids are dextrin behenate, dextrin laurate, dextrin myristate, dextrin stearate, and mixtures thereof.

Another type of polymer found to be suitable, although not preferred, is alkyl substituted galactomannan available from Hercules under their trade name N-HANCE AG.

Alternative organic polymer thickening agents comprise block copolymers of styrene with an alkylene containing up to 5 carbons being a mono or diene, or mixtures thereof, such as ethylene, propylene, butylene and isoprene. Triblock copolymers are especially desirable, including SEBS copolymers.

Fibre-forming Structurant

A number of organic compounds are known to possess the ability to gel hydrophobic organic liquids such as water-immiscible hydrocarbon and/or silicone oils. Such materials are generally monomers or dimers with molecular weight below 10,000 often below 5,000 rather than polymers with more than five repeat units or with molecular weight above 10,000.

Gel formation takes place as an exothermic event within a temperature range referred to as the gel point; upon reheating, melting of the gel takes place as an endothermic event within a temperature range. Such gels can be disrupted by shearing. Although a small partial recovery may then be observed, such gels do not recover their structure for a long time, if at all, unless remelted.

Materials with this property have been reviewed by Terech and Weiss in "Low Molecular Mass Gelators of Organic Liquids and the Properties of their Gels" Chem. Rev 97, 3133–3159 [1997] and by Terech in Chapter 8, "Low-molecular weight Organogelators" of the book "Specialist surfactants" edited by I D Robb, Blackie Academic Professional, 1997.

It is characteristic of such structurants, useful in this invention, that they are able to gel the organic liquid in the absence of any disperse phase the structured liquids are obtainable by cooling from an elevated temperature at which the structurant is in solution in the liquid—this solution being mobile and pourable the structured liquid becomes more mobile if subjected to shear or stress the structure does not spontaneously recover within 24 hours if the sheared liquid is left to stand at ambient laboratory temperature, even though a small partial recovery may be observed the structure can be recovered by reheating to a temperature at which the structurant is in solution in the liquid and allowing it to cool back to ambient laboratory temperature.

It appears that such structurants operate by interactions which are permanent unless disrupted by shear or heating. Such structurants form a network of strands or fibres extending throughout the gelled liquid. In some cases these fibres can be observed by electron microscopy, although in other cases the observation of the fibres which are believed to be present is prevented by practical difficulties in preparing a suitable specimen. When observed, the primary fibres in a gel are generally thin (diameter less than $0.5\mu$, often less than $0.2\mu$) and appear to have numerous branches or interconnections. Primary fibres may entwine to form a thicker strand.

If these fibres are crystalline, they may or may not be the same polymorph as macroscopic crystals obtained by conventional crystallization from a solvent.

One material which is well known to form such gels is 12-hydroxy stearic acid which is discussed in Terech et al "Organogels and Aerogels of Racemic and Chiral 12-hydroxy octadecanoic Acid", Langmuir Vol 10, 3406–3418, 1994. The material is commercially available from Ajinomoto and also from Caschem.

U.S. Pat. No. 5,750,096 is one of several documents which teaches that gelation can be brought about using esters or amides of 12-hydroxy stearic acid. The alcohol used to form such an ester or the amine used to form such an amide may contain an aliphatic, cycloaliphatic or aromatic group with up to 22 carbons therein. If the group is aliphatic it preferably contains at least three carbon atoms. A cycloaliphatic group preferably contains at least five carbon atoms and may be a fixed ring system such as adamantyl.

Other fatty acids with $C_8$ or longer alkyl chains may be used and amides thereof can also be used. A specific example is lauric monoethanolamide also termed MEA lauramide.

N-acyl amino acid amides and esters are also known to structure liquids. We have established that they do so by forming fibrous networks. They are described in U.S. Pat. No. 3,969,087. N-Lauroyl-L-glutamic acid di-n-butylamide is commercially available from Ajinomoto under their designation GP-1.

Further materials which have been disclosed as gelling agents are the amide derivatives of di and tribasic carboxylic acids set forth in WO 98/27954 notably alkyl N,N'dialkyl succinamides.

Lanosterol, as disclosed in U.S. Pat. No. 5,635,165 may suitably be used if the water-immiscible liquid is silicone oil and provided the polymeric thickener is sufficiently soluble therein.

Lanosterol has the following chemical formula:

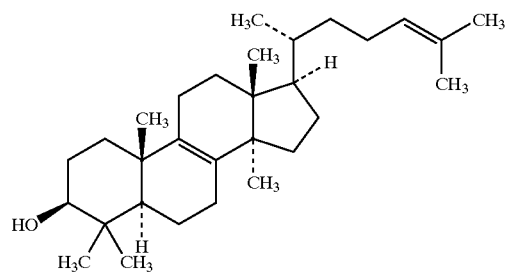

It is commercially available, eg from Croda Chemicals Ltd, and as supplied it contains some dihydrolanosterol. This impurity in the commercial material does not need to be removed.

A novel structurant which is the subject of a co-pending application is a combination of a sterol and a sterol ester.

In its preferred form the sterol satisfies either of the two formulae:

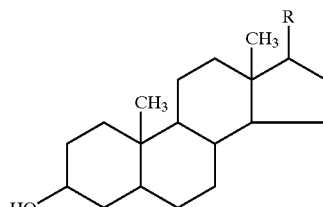

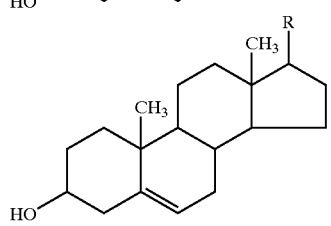

in which R represents an aliphatic, cycloaliphatic or aromatic group, and preferably a linear or branched aliphatic saturated or unsaturated hydrocarbon group. R desirably contains from 1 to 20 carbons and preferably from 4 to 14 carbons.

It is particularly suitable to employ β sitosterol or campesterol or cholesterol, or a hydrogenated derivative thereof, such as dihydrocholesterol, or a mixture of two or more of them. An especially preferred sterol is β-sitosterol.

The preferred sterol ester is oryzanol, sometimes referred to as γ-oryzanol which contains material satisfying the following formula:

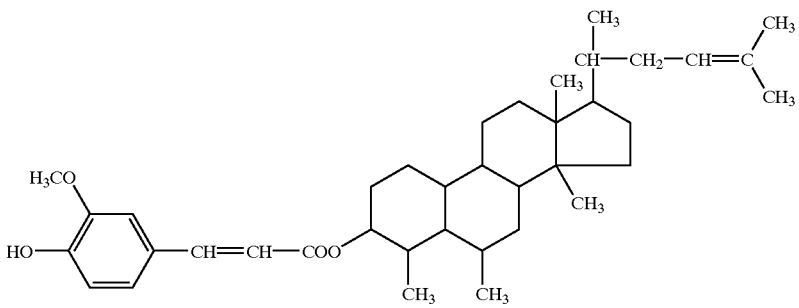

The sterol and sterol ester are used in a mole ratio that is normally selected in the range of from 10:1 to 1:10, especially from 6:1 to 1:4 and preferably in the range of from 3:1 to 1:2. Employment of the two system constituents within such a mole ratio range, and especially within the preferred range facilitates the co-stacking of the constituents and consequently facilitates the formation of a network that is readily able to structure the formulation.

Another novel structurant which is the subject of a co-pending application and which may be used in this invention is an ester of cellobiose and a fatty acid, preferably of 6 to 13 carbon atoms especially 8 to 10 carbon atoms. Preferably the cellobiose is fully esterified, or nearly so, and is in the α-anomeric form.

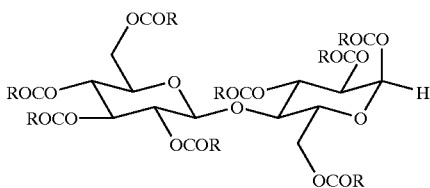

The structure of such a compound, in its α-anomeric form is: where R is an alkyl or alkenyl chain of 5 to 12 carbon atoms so that the acyl group contains 6 to 13 carbon atoms. Particularly preferred acyl groups incorporate a linear alkyl chain of 7 to 10 carbon atoms and are thus octanoyl, nonanoyl, decanoyl or undecanoyl.

The acyl groups may have a mixture of chain lengths but it is preferred that they are similar in size and structure. Thus it is preferred that all of the acyl groups are aliphatic and at least 90% of the acyl groups have a chain length within a range such that the shorter and longer chain lengths in the range differ by no more than two carbon atoms, i.e. length in a range from m−1 to m+1 carbon atoms where m has a value in a range from 7 to 10.

Linear aliphatic acyl groups may be obtained from natural sources, in which case the number of carbon atoms in the acyl group is likely to be an even number or may be derived synthetically from petroleum as the raw material in which case both odd an even numbered chain lengths are available. Synthetic methods for the esterification of saccharides are well known. The esterification of cellobiose has been reported by Takada et al in *Liquid Crystals*, (1995) Volume 19, pages 441–448. This article gives a procedure for the production of the alpha anomers of cellobiose octa-alkanoates by esterification of β-cellobiose using an alkanoic acid together with trifluoracetic anhydride.

A further example of structurant which is the subject of a co-pending application is compounds of the following general structure (I):

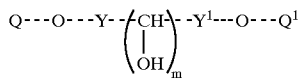

It is preferred that m is 2 so that the structurant compounds comply with a general formula (T1):

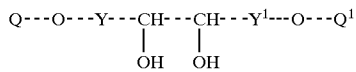

The groups Y and $Y^1$ will usually be identical, i.e. both methylene or both carbonyl. The groups Q and $Q^1$ may not be the same but often will be identical to each other.

If m is 2 and Y and $Y^1$ are methylene groups, the compound is a derivative of threitol, which is 1,2,3,4-tetrahydroxybutane, while if m is 2 and Y and $Y^1$ are carbonyl groups, the compound is a diester of tartaric acid, which is 2,3-dihydroxybutane-1,4-dioic acid.

It is preferred that each group Q and $Q^1$ contains an aromatic nucleus which may be phenyl or, less preferably, some other aromatic group. Thus Q and $Q^1$ may be groups of the formula:

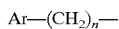

where Ar denotes an aromatic nucleus, notably phenyl or substituted phenyl and n is from 0 to 10.

An aromatic nucleus (Ar) is preferably unsubstituted or substituted with one or more substituents selected from alkyl, alkyloxy, hydroxy, halogen or nitro. One substituent may be an alkyl or alkyloxy group with a long alkyl chain. Thus a formula (T2) for preferred structurants of this invention can be given as:

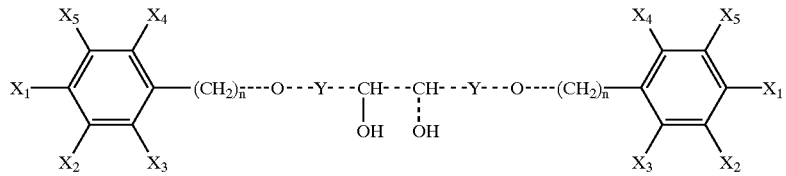

where n=0 to 10, preferably 0 to 3, more preferably 1, 2 or 3;

Y=—$CH_2$— or >C=O $X_1$=H, Cl, Br, F, OH, $NO_2$, O—R, or R, where R is an aliphatic hydrocarbon chain with 1 to 18 carbon atoms;

$X_2$ to $X_5$ are each independently H, Cl, Br, F, OH, $NO_2$, $OCH_3$, or $CH_3$.

In these formulae above, the central carbon atoms which bear hydroxy groups are chiral centres. Thus if m=2, Y and $Y^1$ are the same and Q and $Q^1$ are the same, the compounds will exist as R,R and S,S optically active forms as well as an optically inactive R,S form.

These compounds may be used as their optically active R,R or S,S forms or as a mixture of the two—which may be a racemic mixture.

Compounds within the general formulae (T1 and T2) above are available commercially. Also, syntheses of these compounds have been given in scientific literature where the compounds were being used as intermediates for purposes not related to the present invention. Thus syntheses of threitol derivatives can be found in:

Kataky et al, J. Chem Soc Perkin Trans vol 2 page 321 [1990] Tamoto et al, Tetrahedron Vol 40 page 4617 [1984], and Curtis et al, J.C.S. Perkin I Vol 15 page 1756 [1977]. Preparations of tartrate esters are found at: Hu et al J. Am. Chem. Soc. Vol 118, 4550 [1996] and Bishop et al J. Org Chem Vol 56 5079 [1991].

Amounts of Structurant and Polymer

As already mentioned the amount of fibre-forming structurant is preferably enough to gel the water-immiscible liquid to a shape-sustaining form, even without polymer. The amount of polymer will preferably be enough to thicken the liquid to a viscous state in the absence of fibre-forming structurant.

The amount of fibre-forming structurant will usually be at least 2% or 3%, more preferably at least 5% by weight of the composition. The amount of polymeric thickener will usually be at least 0.2%, in many instances at least 0.3% and often at least 0.5% or 1% by weight of the composition.

The amount of fibre-forming structurant may lie in a range up to 10% more preferably not above 8% by weight of the composition. In other formulations according to the present invention, the amount of fibre-forming structurant may lie in a range up to 15%, such as from 10 to 12% by weight of the composition.

The amount of polymeric thickener may be up to 15% by weight but preferably the polymer is sufficiently effective as a thickener that amounts up to 10% are sufficient. Suitable amounts of polymeric thickener which is one or more polysaccharides esterified with a monocarboxylic acid of 8 to 22 carbon atoms may be in the range from 0.5 to 1% up to 5% or 6% by weight of the composition.

The total amount of the fibre-forming structurant and polymeric thickener will often lie in a range from 3% or 4% by weight of the composition up to 12%, 15%, 16% or 18%.

The percentage by weight of fibre-forming structurant will generally be greater than the percentage by weight of polymer. In many formulations, the weight ratio of the fibre-forming structurant to the polymeric thickener will be at least 2:1 and in many formulations at least 5:1. Commonly, this weight ratio is not more than 40:1 and in many formulations is up to 30:1. In formulations containing a dextrin fatty acid ester, the ratio is often from 5:1 to 20:1 and in formulations containing a block copolymer as described hereinabove, the ratio is often from 10:1 to 30:1.

Liquid Disperse Phase

If the composition is an emulsion, it will contain a solution of an active ingredient as a liquid disperse phase. The disperse phase in an emulsion is hydrophilic. It normally comprises water as solvent and can comprise one or more water soluble or water miscible liquids in addition to or replacement for water. The proportion of water in an emulsion embodying the present invention is often selected in the range of up to 60%, and particularly from 10% up to 40% or 50% of the whole formulation.

One class of water soluble or water-miscible liquids comprises short chain monohydric alcohols, e.g. $C_1$ to $C_4$ and especially ethanol or isopropanol, which can impart a deodorising capability to the formulation. A further class of hydrophilic liquids comprises diols or polyols preferably having a melting point of below 40° C., or which are water miscible. Examples of water-soluble or water-miscible liquids with at least one free hydroxy group include ethylene glycol, 1,2-propylene glycol, 1,3-butylene glycol, hexylene glycol, diethylene glycol, dipropylene glycol, 2-ethoxyethanol, diethylene glycol monomethylether, triethyleneglycol monomethylether and sorbitol. Especially preferred are propylene glycol and glycerol.

In an emulsion the disperse phase is likely to constitute from 5 to 80 or 85% of the weight of the composition preferably from 5 to 50 or 65% more preferably from 25 or 35% up to 50 or 65%, while the continuous phase with the structurant therein provides the balance from 15 or 35% up to 95% of the weight of the composition. Compositions with high proportion of disperse phase, i.e. from 65 to 85% disperse phase, may also be advantageous. They can give good hardness even though the structured continuous phase is only a small percentage of the total composition.

An emulsion composition will generally include one or more emulsifying surfactants which may be anionic, cationic, zwitterionic and/or nonionic surfactants. The proportion of emulsifier in the composition is often selected in the range up to 10% by weight and in many instances from 0.1 or 0.25 up to 5% by weight of the composition. Most preferred is an amount from 0.1 or 0.25 up to 3% by weight. Nonionic emulsifiers are frequently classified by HLB value. It is desirable to use an emulsifier or a mixture of emulsifiers with an overall HLB value in a range from 2 to 10 preferably from 3 to 8.

It may be convenient to use a combination of two or more emulsifiers which have different HLB values above and below the desired value. By employing the two emulsifiers together in appropriate ratio, it is readily feasible to attain a weighted average HLB value that promotes the formation of an emulsion.

Many suitable emulsifiers of high HLB are nonionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditol as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons. The hydrophobic moiety can be either linear or branched and is often saturated, though it can be unsaturated, and is optionally fluorinated. The hydrophobic moiety can comprise a mixture of chain lengths, for example those deriving from tallow, lard, palm oil, sunflower seed oil or soya bean oil. Such nonionic surfactants can also be derived from a polyhydroxy compound such as glycerol or sorbitol or other alditols.

Examples of emulsifiers include ceteareth-10 to 25, ceteth-10–25, steareth-10–25 (i.e. $C_{16}$ to $C_{18}$ alcohols ethoxylated with 10 to 25 ethylene oxide residues) and PEG-15–25 stearate or distearate. Other suitable examples include $C_{10}$–$C_{20}$ fatty acid mono, di or tri-glycerides. Further examples include $C_{18}$–$C_{22}$ fatty alcohol ethers of polyethylene oxides (8 to 12 EO).

Examples of emulsifiers, which typically have a low HLB value, often a value from 2 to 6 are fatty acid mono or possibly diesters of polyhydric alcohols such as glycerol, sorbitol, erythritol or trimethylolpropane. The fatty acyl moiety is often from $C_{14}$ to $C_{22}$ and is saturated in many. instances, including cetyl, stearyl, arachidyl and behenyl. Examples include monoglycerides of palmitic or stearic acid, sorbitol mono or diesters of myristic, palmitic or stearic acid, and trimethylolpropane monoesters of stearic acid.

A particularly desirable class of emulsifiers comprises dimethicone copolymers, namely polyoxyalkylene modified dimethylpolysiloxanes. The polyoxyalkylene group is often a polyoxyethylene (POE) or polyoxypropylene (POP) or a copolymer of POE and POP. The copolymers often terminate in $C_1$ to $C_{12}$ alkyl groups.

Suitable emulsifiers and co-emulsifiers are widely available under many trade names and designations including Abil™, Arlacel™, Brij™, Cremophor™, Dehydrol™, Dehymuls™, Emerest™, Lameform™, Pluronic™, Prisorine™, Quest PGPH™, Span™, Tween™, SF1228, DC3225C and Q2-5200.

Antiperspirant Actives

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates.

Aluminium halohydrates are usually defined by the general formula $Al_2(OH)_xQ_y \cdot wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever NV et al), the contents of which specification is incorporated herein by reference. Some activated salts do not retain their enhanced activity in the presence of water but are useful in substantially anhydrous formulations, i.e. formulations which do not contain a distinct aqueous phase.

Zirconium actives can usually be represented by the empirical general formula: $ZrO(OH)_{2n-nz}B_z \cdot wH_2O$ in which z is a variable in the range of from 0.9 to 2.0 so that the value 2n–nz is zero or positive, n is the valency of B, and B is selected from the group consisting of chloride, other halide, sulphamate, sulphate and mixtures thereof. Possible hydration to a variable extent is represented by $wH_2O$. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have coordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_2(NH_2)COOH$.

It is highly desirable to employ complexes of a combination of aluminium halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis.

Other actives which may be utilised include astringent titanium salts, for example those described in GB 2299506A.

The weight of solid antiperspirant salt in a composition which is a suspension of particulate solid normally includes the weight of any water of hydration and any complexing agent that may also be present in the solid active.

In a composition in which antiperspirant active in particulate form is suspended in the water-immiscible liquid carrier, the particle size of the antiperspirant salts often falls within the range of 0.1 to 200 μm with a mean particle size often from 3 to 20 μm. Both larger and smaller mean particle sizes can also be contemplated such as from 20 to 50 μm or 0.1 to 1 μm or up to 3 μm.

If the composition is in the form of an emulsion the antiperspirant active will be dissolved in the disperse phase and the weight of antiperspirant active in the composition is taken as the weight of solid active salt excluding any water or solvent present. In this case, the antiperspirant active will often provide from 3 to 60% by weight of the disperse phase, particularly from 10% or 20% up to 55% or 60% of that phase.

Optional Ingredients

Optional ingredients in compositions of this invention can include disinfectants, for example at a concentration of up to about 10% w/w. Suitable deodorant actives can comprise deodorant effective concentrations of antiperspirant metal salts, deoperfumes, and/or microbicides, including particularly bactericides, such as chlorinated aromatics, including biguanide derivatives, of which materials known as Igasan DP300™, Triclosan, Tricloban™, and Chlorhexidine warrant specific mention. A yet another class comprises biguanide salts such as available under the trade mark Cosmosil™.

Other optional ingredients include wash-off agents, often present in an amount of up to 10% w/w to assist in the removal of the formulation from skin or clothing. Such wash-off agents are typically nonionic surfactants such as esters or ethers containing a $C_8$ to $C_{22}$ alkyl moiety and a hydrophilic moiety which can comprise a polyoxyalkylene group (POE or POP) and/or a polyol. A possible optional ingredient is a wax, as defined earlier, desirably in a small amount not exceeding 3% by weight of the composition.

The compositions herein can incorporate one or more cosmetic adjuncts conventionally envisaged for antiperspirant soft solids. Such cosmetic adjuncts can include skin feel improvers, such as talc or finely divided polyethylene, for example in an amount of up to about 10%; skin benefit agents such as allantoin or lipids, for example in an amount of up to 5%; colours; skin cooling agents other than the already mentioned alcohols, such a menthol and menthol derivatives, often in an amount of up to 2%, all of these percentages being by weight of the composition. A commonly employed adjunct is a perfume, which is normally present at a concentration of from 0 to 4% and in many formulations from 0.25 to 2% by weight of the composition.

Ethanol gives a cooling effect on application to skin, because it is very volatile. It is preferred that the content of ethanol or any monohydric alcohol with a vapour pressure above 1.3 kPa (10 mmHg) is not over 15% better not over 8% by weight of the composition.

Translucent/Transparent Compositions

If a composition of this invention is formulated as an emulsion it is possible to construct the formulation such that the emulsion is translucent or transparent. In order to do this the refractive indices of the water-immiscible continuous phase and the polar or aqueous disperse phase must be matched to each other and the value of refractive index at which they are matched must also approximately match the refractive index of the fibre-forming structurant.

The refractive index of a fibrous network of a structurant can be determined by using that structurant to gel a number of oils or oil mixtures of differing refractive index. When the resulting gel is transparent, the refractive index of the oil or oil mixture(which can be determined by conventional measurement) is a good approximation to the refractive index of the structurant. The oils or mixtures of oils should be chosen from those which are gelled well by the structurant to avoid interfering effects.

Some examples of oils which may be used to make mixtures which vary in refractive index and used for the purpose of such measurement are:

volatile silicone (refractive index about 1.40)

$C_{12-15}$ alkyl benzoate (refractive index about 1.48) which is available as Finsolv TN and/or octylmethoxycinnamate (refractive index about 1.54) which is available as Parsol MCX Polyphenylsiloxane (DC710) (refractive index about 1.53).

Cinnamic aldehyde (refractive index about 1.62).

Using this method we have determined the refractive indices of some structurants, namely:

| | |
|---|---|
| N-lauroyl L-glutamic acid di-n-butylamide | approx 1.48 |
| 12-hydroxystearic acid | approx 1.52 |
| α-cellobiose octa-esters with $C_8$ to $C_{12}$ fatty acids | approx 1.48 |

It appears that polymeric thickeners often cause little scattering of light and do not generally need to be taken separately into account for refractive index matching. For the continuous phase, silicon-free water-immiscible liquid oils generally have refractive indices in a range from 1.43 to 1.49 at 22° C. and can be used alone or mixed together to give a silicon-free carrier liquid with refractive index in this range. Volatile silicone oils generally have a refractive index slightly below 1.40 at 22° C., but carrier liquid mixtures with refractive indices in the range from 1.41 to 1.46 can be obtained by mixing limited amounts of volatile silicone with other oils. Cosmetically acceptable non-volatile silicone oils generally have refractive indices in a range from 1.45 to 1.48 at 22° C. and so can be included when desired.

The refractive index of the continuous phase will be very close to the refractive index of the carrier liquid (usually a carrier liquid mixture) which is its principal component. The polymeric thickener and any minor ingredients dissolved in the carrier liquid will affect its refractive index, but their effect will usually be small.

For the disperse phase, a solution of an antiperspirant active salt in water alone will generally display a refractive index below 1.425. The refractive index can be raised by incorporating a diol or polyol into the aqueous solution.

For the regular production of compositions with optimum transparency it may prove desirable to monitor the refractive indices of the raw materials to detect any batch to batch variation. If necessary the composition of a liquid phase can be adjusted by variations in the quantity of a constituent material.

For a composition which is a suspension the route to a transparent or translucent composition is to match the refractive indices of the liquid carrier and the suspended solid to that of the fibre-forming structurant. Particulate antiperspirant actives which are anhydrous solids generally have a refractive index substantially above 1.50 which is brought down by hydration, but we have found that it is not easy to obtain an antiperspirant active with a refractive index of 1.48 or below even if the active is partially hydrated to lower its refractive index. Therefore it is possible, but more difficult, to match refractive indices within a composition which is a suspension of particulate solid antiperspirant active.

Although compositions of this invention may be translucent or opaque when seen in bulk, they are nevertheless able to give a low visible residue when applied to skin or transferred to fabric.

Product Packages

A composition of this invention will usually be marketed as a product comprising a container with a quantity of the composition therein, where the container has at least one aperture for the delivery of composition, and means for urging the composition in the container towards the delivery aperture. Conventional containers take the form of a barrel of oval cross section with the delivery aperture(s) at one end of the barrel.

A composition of this invention is preferably sufficiently rigid that it is not apparently deformable by hand pressure, even though a surface layer will transfer as a film to skin, and is suitable for use as a stick product in which a quantity of the composition in the form of a stick is accommodated within a container barrel having an open end at which an end portion of the stick of composition is exposed for use. The opposite end of the barrel is closed.

Generally the container will include a cap for its open end and a component part which is sometimes referred to as an elevator or piston fitting within the barrel and capable of relative axial movement along it. The stick of composition is accommodated in the barrel between the piston and the open end of the barrel. The piston is used to urge the stick of composition along the barrel. The piston and stick of composition may be moved axially along the barrel by manual pressure on the underside of the piston using a finger or rod inserted within the barrel. Another possibility is that a rod attached to the piston projects through a slot or slots in the barrel and is used to move the piston and stick. Preferably the container also includes a transport mechanism for moving the piston comprising a threaded rod which extends axially into the stick through a correspondingly threaded aperture in the piston, and means mounted on the barrel for rotating the rod. Conveniently the rod is rotated by means of a handwheel mounted on the barrel at its closed end, i.e. the opposite end to the delivery opening.

The component parts of such containers are often made from thermoplastic materials, for example polypropylene or polyethylene. Descriptions of suitable containers, some of which include further features, are found in U.S. Pat. Nos. 4,865,231, 5,000,356 and 5,573,341.

Preparation

Compositions of this invention can be produced by conventional processes. Such processes involve forming a heated mixture of the composition at a temperature which is sufficiently elevated that all the polymeric thickener and gelating structurant dissolves, introducing antiperspirant active, then pouring or otherwise introducing that mixture into a mould, which may be a dispensing container, and then cooling the mixture.

A convenient process sequence for a composition which is a suspension comprises first forming a solution of the polymer and other structurant in the water-immiscible liquid or liquid mixture. This is normally carried out by agitating the mixture at a temperature sufficiently high that all the structurant dissolves (the dissolution temperature) such as a temperature in a range from 50 to 120° C. Thereafter the particulate constituent, for example particulate antiperspirant active, is blended with the hot mixture. This must be done slowly, or the particulate solid must be preheated, in order to avoid premature gelation. The resulting blend is then introduced into a dispensing container such as a stick barrel. This is usually carried out at a temperature 5 to 30° C. above the setting temperature of the composition. The container and contents are then cooled to ambient temperature. Cooling may be brought about by nothing more than allowing the container and contents to cool. Cooling may be assisted by blowing ambient or even refrigerated air over the containers and their contents.

In a suitable procedure for making emulsion formulations, a solution of the structurant in the water-immiscible liquid phase is prepared at an elevated temperature just as for suspension sticks. If any emulsifier is being used, this is conveniently mixed into this liquid phase. Separately an aqueous or hydrophilic disperse phase is prepared by introduction of antiperspirant active into the liquid part of that phase (if this is necessary: antiperspirant actives can sometime be supplied in aqueous solution which can be utilised as is). If possible, this solution of antiperspirant active which will become the disperse phase is preferably heated to a temperature similar to that of the continuous phase with structurant therein, but without exceeding the boiling point of the solution, and then mixed with the continuous phase. Alternatively, the solution is introduced at a rate which maintains the temperature of the mixture. If it is necessary to work at a temperature above the boiling temperature of the disperse phase, or at a temperature where evaporation from this phase is significant, a pressurised apparatus could be used to allow a higher temperature to be reached. With the structurant materials of this invention this is usually unnecessary. After the two phases are mixed, the resulting mixture is filled into dispensing containers, typically at a temperature 5 to 30° C. above the setting temperature of the composition, and allowed to cool as described above for suspension sticks.

Measurement of Properties i) Penetrometer

The hardness and rigidity of a composition which is a firm solid can be determined by penetrometry. If the composition is a softer solid, this will be observed as a substantial lack of any resistance to the penetrometer probe.

A suitable procedure is to utilises a lab plant PNT penetrometer equipped with a Seta wax needle (weight 2.5 grams) which has a cone angle at the point of the needle specified to be 9°10'±15'. A sample of the composition with a flat upper surface is used. The needle is lowered onto the surface of the composition and then a penetration hardness measurement is conducted by allowing the needle with its holder to drop under a total weight, (i.e. the combined weight of needle and holder) of 50 grams for a period of five seconds after which the depth of penetration is noted.

Desirably the test is carried out at a number of points on each sample and the results are averaged. Utilising a test of this nature, an appropriate hardness for use in an open-ended dispensing container is a penetration of less than 30 mm in this test, for example in a range from 2 to 30 mm. Preferably the penetration is in a range from 5 mm to 20 mm. A penetration of no more than 30 mm better no more than 20 mm in this test may be taken as characteristic of a firm composition.

It is preferred that if the polymeric thickener is omitted from the composition, so that it is structured by the fibre-forming gelating structurant, the penetration in this test is not more than 30 mm.

A test composition consisting of the water-immiscible liquid and the fibre-forming gelating structurant only, in the same proportions as in a complete composition of this invention, may display a penetration of no more than 30 mm in this test. In a specific protocol for this test, a test composition was prepared as a stick, and measurements on a stick were performed in the stick barrel. The stick was wound up to project from the open end of the barrel, and then cut off to leave a flat, uniform surface. The needle was carefully lowered to the stick surface, and then a penetration hardness measurement was conducted. This process was carried out at six different points on the stick surface. The hardness reading quoted is the average value of the 6 measurements.

ii) Deposition

Another test of the properties of a composition is the amount of the composition which is delivered onto a surface when the composition is drawn across that surface (representing the application of a stick product to human skin). To carry out this test of deposition, a sample of the composition with standardised shape and size is fitted to apparatus which draws the sample across a test surface under standardised conditions. The amount transferred to the surface is determined as an increase in the weight of the substrate to which it is applied. If desired the colour, opacity or clarity of the deposit may subsequently be determined.

A specific procedure for such tests used apparatus to apply a deposit from a stick onto a substrate under standardised conditions and then measures the mean level of white deposits using image analysis.

The substrates used were:

a: 12×28 cm strip of grey abrasive paper (3M™ P800 WetorDry™ Carborundum paper)

b: 12×28 cm strip of black Worsted wool fabric.

The substrates were weighed before use. The sticks were previously unused and with domed top surface unaltered.

The apparatus comprised a flat base to which a flat substrate was attached by a clip at each end. A pillar having a mounting to receive a standard size stick barrel was mounted on an arm that was moveable horizontally across the substrate by means of a pneumatic piston.

Each stick was kept at ambient laboratory temperature overnight before the measurement was made. The stick was advanced to project a measured amount from the barrel. The barrel was then placed in the apparatus and a spring was positioned to biassed the stick against the substrate with a standardised force. The apparatus was operated to pass the stick laterally across the substrate eight times. The substrate was carefully removed from the rig and reweighed.

iii) Whiteness of Deposit

The deposits from the previous test were assessed for their whiteness after an interval of 24 hours approximately. This was done using a Sony $XC_{77}$ monochrome video camera with a Cosmicar 16 mm focal length lens positioned vertically above a black table illuminated from a high angle using fluorescent tubes to remove shadowing. The apparatus was initially calibrated using a reference grey card, after the fluorescent tubes had been turned on for long enough to give a steady light output. A cloth or Carborundum paper with a deposit thereon from the previous test was placed on the table and the camera was used to capture an image. An area of the image of the deposit was selected and analysed using a Kontron IBAS image analyser. This notionally divided the image into a large array of pixels and measured the grey level of each pixel on a scale of 0 (black) to 255 (white). The average of the grey intensity was calculated. This was a measure of the whiteness of the deposit, with higher numbers indicating a whiter deposit. It was assumed that low numbers show a clear deposit allowing the substrate colour to be seen.

iv) Light transmission

The translucency of a composition may be measured by placing a sample of standardised thickness in the light path of a spectrophotometer and measuring transmittance, as a percentage of light transmitted in the absence of the gel.

We have carried out this test using a dual-beam spectrophotometer. The sample of composition was poured hot into a 4.5 ml cuvette made of polymethylmethacrylate (PMMA) and allowed to cool to an ambient temperature of 20–25° C. Such a cuvette gives a 1 cm thickness of composition. Measurement was carried out at 580 nm, with an identical but empty cuvette in the reference beam of the spectrophotometer, after the sample in the cuvette had been held for 24 hours. We have observed that a composition which gives a transmittance of as little as 1% in this test is perceived by eye as "translucent". If a stick is made from a composition with 3% transmittance, it is possible to see cavities made by boring beneath the surface of the sample. By contrast, a conventional stick structure with stearyl alcohol is so opaque that it is impossible to see beneath its surface. A transmittance measured at any temperature in the range from 20–25° C. is usually adequately accurate, but measurement is made at 22° C. if more precision is required.

EXAMPLES

The examples and comparative examples below were prepared using a number of materials set out with their proprietary names in the following list. All temperatures are in degrees Celsius.
1) Volatile cyclic silicone (cyclomethicone) DC 245(Dow Corning)
2) Octyldodecanol (Eutanol G from Henkel)
3) N-lauryl-L-glutamic acid di-n-butylamide (GP1 from Ajinomoto)
4) Rheopearl KL from Chiba Flour Milling Co
5) β-sitosterol (available as ultrasitosterol from Kaukas)
6) γ-oryzanol (from Jan Dekker (UK) Ltd)
7) C12–15 alkyl benzoate (Finsolv TN from Fintex)
8) Al/Zr tetrachlorohydrex glycine complex (WZR 30 DM HBD from Westwood, also known as Westchlor 30B DM HBD)
9) Al/Zr Tetrachlorohydrex glycine complex (AZAG 7167 from Summit)
10) Suprafino talc (particle size about 5μ) from Cyprus Minerals
11) 12-hydroxystearic acid from Caschem
12) Panalene-L-14E (hydrogenated polyisobutene from Amoco)
13) Isopropyl myristate (abbreviated to IPM from Unichema)
14) Silicone wax ($DC_{2503}$ from Dow Corning)
15) Polydecene (Silkflo 364NF from Albemarle)
16) 40% aqueous solution of Al/Zr pentachlorohydrate (Rezal 67 from Reheis)
17) 50% aqueous solution of Al/Zr pentachlorohydrate (Zirkonal 50 from Giulini)
18) Cetyl dimethicone copolyol (Abil EM90 emulsifier from Th. Goldschmidt)
19) Polyglyceryl-3-diisostearate from Henkel
20) Al/Zr tetrachlorohydrex glycine complex (Rezal 36GP-SUF from Reheis)
21) Thickening agent—block copolymer of styrene with iso-prene (Kraton G1650 from Shell)
22) Cellobiose octanonanoate-preparation following Example 1 of WO 00/61079.

Examples 1 to 3 and comparative Example 4 are all antiperspirant suspension sticks prepared using a mixture of water-immiscible liquids, an antiperspirant active, a fibre-forming structurant compound or system and (for examples of the invention) a thickening polymer.

The following general method of preparation was used for these examples and comparative examples. A solution of the thickening polymer (when employed) and other structurants in the organic liquid(s) was made by mixing these materials, heating and agitating the mixture at a temperature sufficiently high that the polymer and other structurants all dissolve. The mixture was then allowed to cool to 80–85° C. before the antiperspirant active was added. The mixture was next allowed to cool to 5–20° C. above its gelling temperature (determined in a preliminary experiment) and poured into dispensing containers. These were then left to cool to room temperature.

When GP-1 was used, it was dissolved in the hot liquid mixture before the thickening polymer was added and dissolved. When β-sitosterol and oryzanol were used in combination as structurant, the oryzanol was first dissolved in the hot liquid mixture followed by addition and dissolution of the thickening polymer, and β-sitosterol. The sticks were tested by penetrometer and for whiteness of deposits by the test procedures given earlier.

| Examples | 1.1 comparative | 1.2 | 1.3 |
|---|---|---|---|
| | Parts by weight | | |
| GP1 (3) | 5 | 5 | 5 |
| Dextrin Palmitate (4) | 0 | 2 | 2 |
| Cyclomethicone DC 245 (1) | 55 | 53 | 51 |
| Octyldodecanol (2) | 13.25 | 13.25 | 13.25 |
| Perfume | 0.75 | 0.75 | 0.75 |
| AZAG (8) | 26 | 26 | 26 |
| Talc (10) | 0 | 0 | 2 |
| | Properties | | |
| penetration depth (mm) | 9.2 | 7.2 | 4.9 |
| Whiteness on grey paper (initial) | 30 | 30 | 30 |
| Whiteness on grey paper after 24 hours | 35 | 36 | 38 |
| Whiteness on black wool (initial) | 33 | 31 | 26 |
| Whiteness on black wool after 24 hours | 87 | 90 | 72 |

1.2 shows an increase in hardness compared to 1.1, without detriment to visible residue. 1.3 shows the possibility of additionally adding talc without detriment to visible residues.

Example 2

| Examples | 2.1 Comp | 2.2 | 2.3 Comp | 2.4 |
|---|---|---|---|---|
| | Percent by weight | | | |
| Beta Sitosterol (5) | 2.4 | 2.4 | 2.4 | 2.4 |
| Oryzanol (6) | 3.6 | 3.6 | 3.6 | 3.6 |
| Dextrin Palmitate (4) | 0 | 1 | 0 | 2 |
| Cyclomethicone DC 245 (1) | 40.8 | 40.2 | 54.4 | 52.8 |
| $C_{12-15}$ Alkyl Benzoate (7) | 27.2 | 26.8 | 13.6 | 13.2 |
| AZAG (Q5 - 7167) (9) | 24 | 24 | 24 | 24 |
| Talc (10) | 2 | 2 | 2 | 2 |
| PROPERTIES | | | | |
| penetration depth (mm) | 9.7 | 7.4 | 20.4 | 6.7 |
| Whiteness on grey paper (initial) | 26.9 | 23.3 | * | 26.0 |
| Whiteness on grey paper 24 hours after deposition | 26.2 | 32.3 | * | 25.7 |
| Whiteness on black wool (initial) | 35.7 | 16.7 | * | 22.4 |
| Whiteness on black wool after 24 hours | 28.6 | 9.5 | * | 14.2 |

| Examples | 2.5 Comp | 2.6 | 2.7 Comp | 2.8 |
|---|---|---|---|---|
| | Percent by weight | | | |
| Beta Sitosterol (5) | 2.4 | 2.4 | 1.6 | 1.6 |
| Oryzanol (6) | 3.6 | 3.6 | 2.4 | 2.4 |
| Dextrin Palmitate (4) | 0 | 2 | 0 | 1 |
| 12-hydroxystearic acid (11) | 0 | 0 | 6 | 6 |
| Cyclomethicone DC 245 (1) | 47.6 | 46.2 | 37.2 | 36.6 |
| $C_{12-15}$ Alkyl Benzoate (7) | 20.4 | 19.8 | 24.8 | 24.4 |
| AZAG (Q5 - 7167) (9) | 24 | 24 | 24 | 24 |
| Talc (10) | 2 | 2 | 2 | 2 |
| PROPERTIES | | | | |
| penetration depth (mm) | 10.9 | 6.3 | 9.9 | 9.2 |
| Whiteness on grey paper (initial) | 24.1 | 27.0 | 23.2 | 24.5 |
| Whiteness on grey paper after 24 hours | 28.1 | 26.7 | 15.3 | 32.2 |
| Whiteness on black wool (initial) | 27.9 | 19.0 | 30.9 | 29.3 |
| Whiteness on black wool after 24 hours | 13.8 | 9.7 | 39.1 | 12.4 |

*too soft to measure/apply

In all the formulations of Example 2 incorporation of polymer increases hardness without increasing whiteness.

Examples 2.3 (comparative) and 2.4 were tested for stability at 50° C.—an accelerated test. The composition of Example 2.3 displayed syneresis after 1 day. The composition of Example 2.4 remained stable over 7 days.

| Examples | 3.1 | 3.2 (comparative) |
|---|---|---|
| | Percent by weight | |
| Beta Sitosterol (5) | 2.4 | 3.1 |
| Oryzanol (6) | 3.6 | 3.1 |
| Cyclomethicone DC 245 (1) | 45.7 | 50.5 |
| $C_{12-15}$ Alkyl Benzoate (7) | 19.6 | 19.3 |
| AZAG (Q5 - 7167) (9) | 24 | 24 |
| Dextrin Palmitate (4) | 2 | 0 |
| Talc (10) | 2 | 0 |
| Perfume | 0.7 | 0 |
| PROPERTIES | | |
| penetration depth (mm) | 5.9 | 12 |
| Whiteness on grey paper (initial) | 31 | |
| Whiteness on grey paper after 24 hours | 29 | |
| Whiteness on black wool (initial) | 20 | |
| Whiteness on black wool after 24 hours | 11 | |

These two compositions gave sticks which were opaque.

The two compositions were used for a test of efficacy carried out with a panel of volunteers in a heated environment. During a preliminary preparation period all the panellists used an alcoholic underarm product which is a deodorant but not an antiperspirant. During the test period the panellists used a standard dosage of the product on one underarm and a placebo on the other. The test measurement was made in a room at 40° C. and 40% relative humidity. After a period of 40 minutes each underarm is dried and a pre-weighed absorbent cotton pad is placed in the underarm region. Each panellist remains seated in the room for a further 20 minute period after which the cotton pads are collected and re-weighed. The antiperspirant efficacy (% sweat reduction) is calculated as $$\frac{(W_2 - W_1)}{W_2} \times 100\%$$

where $W_1$ is the weight of sweat collected from underarms treated with the test product and $W_2$ is the weight of sweat collected from underarm regions which have received no treatment.

The results obtained were

Formulation 3.1 (invention): 60.6%

Formulation 3.2 (comparative): 39.0

Comparative Example 4

| Examples | 4.1 | 4.2 | 4.3 |
|---|---|---|---|
| | Percent by weight | | |
| DC2503 (14) | 1 | 0 | 0 |
| 12-hydroxystearic acid (11) | 8 | 8 | 9 |
| Cyclomethicone DC 245 (1) | 47.0 | 47.7 | 47.0 |
| Panalene-L-14E (12) | 9.6 | 9.7 | 9.6 |
| Isopropyl myristate (13) | 14.4 | 14.6 | 14.4 |
| AlZr trichlorohydrex gly (8) | 20 | 20 | 20 |
| Properties | | | |
| Penetration depth (mm) | 14.7 | 11.1 | 12.1 |
| Whiteness on black wool after 24 hours | 27.5 | 26.5 | |

It should be noted that the temperatures for pouring into stick barrels were 2° C. above temperatures at which gelation had been found to occur in an initial trial experiment. The temperatures were close to the range of 60–62° C.

taught in U.S. Pat. No. 5,480,637—Example 15. The penetration depth for Example 4.1 was greater than for Examples 4.2 or 4.3, indicating that the incorporation of the DC 2503 silicone wax did not improve hardness.

Example 5

Emulsion sticks were prepared using the following general method of preparation. A solution of the thickening polymer and other structurants in the organic liquid(s) was made by mixing these materials, heating and agitating the mixture at a temperature sufficiently high that the polymer and other structurants all dissolve. The mixture was then allowed to cool to about 95° C. while stirring with shear. A solution of the antiperspirant active, preheated to 95° C. was added. After stirring with shear at about 95° C. for a further 10 minutes, the mixture was poured into dispensing containers. These were then left to cool to room temperature.

If oryzanol and β-sitosterol were used, the orzyanol was dissolved in the liquids at 60° C. before heating to about 110° C. and adding the β-sitosterol then cooling to about 95° C. to add further ingredients.

| Examples | 5.1 | 5.2 |
|---|---|---|
| | Percent by weight | |
| Beta Sitosterol (5) | 2.50 | 1.62 |
| Oryzanol (6) | 2.50 | 2.40 |
| Dextrin Palmitate (4) | 1.67 | 1.35 |
| Cyclomethicone DC 245 (1) | 29.98 | 30.54 |
| C$_{12-15}$ Alkyl Benzoate (7) | 12.85 | 13.09 |
| Abil EM 90 (18) | 0.50 | — |
| Lameform TGI (19) | — | 1.0 |
| Antiperspirant active solution (16) | 50 | 50 |

| Examples | 5.3 | 5.4 | 5.5 |
|---|---|---|---|
| | Percent by weight | | |
| Beta Sitosterol (5) | 2.50 | 3.20 | |
| Oryzanol (6) | 2.50 | 4.80 | |
| Dextrin Palmitate (4) | 1.67 | 2.67 | 2.4 |
| Cellobiose octanonanoate (22) | | | 3.75 |
| Cyclomethicone DC 245 (1) | 29.98 | 27.18 | 17.3 |
| C$_{12-15}$ Alkyl Benzoate (7) | 12.85 | 11.65 | — |
| Silkflo 364NF (15) | — | — | 26.4 |
| Abil EM 90 (18) | 0.50 | 0.50 | 1.0 |
| Antiperspirant active solution (16) | 50 | 50 | — |
| Antiperspirant active solution (17) | | | 40 |
| Glycerol | | | 10 |

Examples 5.1 to 5.4 were opaque sticks which gave a low visible residue when applied to cloth or carborundum paper in the procedure described above.

The stick of Example 5.5 was translucent. The refractive indices of its continuous and disperse phases were measured as 1.433 at 25° C. The refractive index of cellobiose octanonanoate was determined as 1.48.

The transmittance of the composition was measured in accordance with the method given above and found to be 1.2% at 22° C.

Example and Comparative Example 6

In this Example and Comparative Example, emulsion sticks were prepared by the general method described in Example hereinabove using cellobiose octanoate.

| Example No | 6.A Comp | 6.1 | 6.B Comp | 6.2 | 6.3 |
|---|---|---|---|---|---|
| Kraton G1650 (21) | | 0.5 | | 0.5 | 1.0 |
| Cellobiose Octanonanoate (22) | 10 | 10 | 7.5 | 7.5 | 7.5 |
| DC245 (1) | 7.9 | 7.8 | 8.4 | 8.3 | 8.2 |
| Silkflo 364 (15) | 31.6 | 31.2 | 33.6 | 33.2 | 32.8 |
| Abil EM90 (18) | 0.5 | 0.5 | 0.5 | 0.5 | 0.5 |
| Water | 16 | 16 | 16 | 16 | 16 |
| Glycerol | 9 | 9 | 9 | 9 | 9 |
| Rezal 36GP SUF (20) | 25 | 25 | 25 | 25 | 25 |
| Properties | | | | | |
| Hardness (mm) * | 13.48 | 11.94 | 15.68 | 14.61 | 14.04 |
| Pay-off (g) | 0.488 | 0.466 | 0.571 | 0.559 | 0.469 |

Examples 6.1, 6.2 and 6.3 show that the addition of the thickening polymer increased the hardness of the resultant emulsion stick, and by visual inspection retained acceptable clarity.

We claim:

1. A firm solid antiperspirant composition having a continuous phase comprising water-immiscible liquid containing:
   i) one or more gelating structurant materials which form a network of fibres within the liquid, and
   ii) a polymeric thickener which has an organic polymer backbone containing at least five monomer repeat units, which polymer has the ability to increase the viscosity of the water-immiscible liquid in the absence of the gelating structurant materials; and
   iii) an antiperspirant active dispersed in the continuous phase said composition being free from or containing less than 3% by weight of a fatty alcohol that is solid at 20° C.

2. A composition according to claim 1 which does not contain more than 3% of any material which is solid at 30° C., is molten at 95° C., soluble in the water-immiscible liquid at 95° C., but does not form a network of fibres in the water-immiscible liquid.

3. A composition according to claim 1 wherein the total amount of said fibre-forming structurant (i) and said polymeric thickener (ii) is from 3% to 18% by weight of the composition.

4. A composition according to claim 3 wherein the total amount of said gelating structurant (i) and said polymeric thickener (ii) is from 4% to 16% by weight of the composition.

5. A composition according to claim 1 wherein the total amount of fibre-forming gelating structurant material is from 3% to 15% by weight of the composition.

6. A composition according to claim 1 wherein the percentage of fibre-forming structurant is greater than the percentage of polymeric thickener by weight of the composition.

7. A composition according to claim 7 wherein the fibre forming structurant and polymeric are present in a weight ratio in the range of from 2:1 to 40:1.

8. A composition according to claim 1 wherein the organic polymeric thickener comprises a polysaccharide esterified with a monocarboxylic acid of 8 to 22 carbon atoms.

9. A composition according to claim 8 containing from 0.5% to 5% by weight of the composition of a said esterified polysaccharide.

10. A composition according to claim 8 wherein the esterified polysaccharide is a dextrin fatty acid ester having the formula

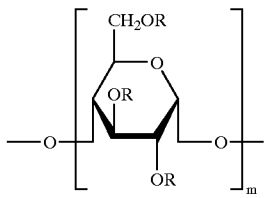

wherein each R group, individually, is a hydrogen or an acyl group of up to 22 carbon atoms, provided that at least one R group per glucose unit is an acyl group of 8 to 22 carbon atoms, and m has a value from about 20 to 30.

11. A composition according to claim 1 wherein the organic polymeric thickener comprises hydrogenated styrene-isoprene copolymer.

12. A composition according to claim 1 characterised in that the water-immiscible liquid contains a volatile silicone and optionally a non-volatile silicone and/or a non-silicone hydrophobic organic liquid selected from hydrocarbons, hydrophobic aliphatic esters, aromatic esters and hydrophobic alcohols.

13. A composition according to claim 1 wherein the water-immiscible liquid contains silicone oil in an amount which is at least 10% by weight of the composition.

14. A composition according to claim 1 wherein the composition is a suspension with a particulate solid material dispersed in said continuous phase.

15. A composition according to claim 1 wherein the composition is an emulsion with a hydrophilic, preferably water-miscible, disperse phase in addition to said water-immiscible liquid continuous phase.

16. A composition according to claim 15 wherein the disperse phase contains a diol or polyol.

17. A composition according to claim 15 which contains from 0.1% to 10% by weight of a nonionic emulsifier.

18. A composition according to according to claim 1 wherein the antiperspirant active comprises an aluminium and/or zirconium halohydrate, an activated aluminium and/or zirconium halohydrate, or an aluminium and/or zirconium complex or an activated aluminium and/or zirconium complex.

19. A composition according to claim 18 wherein the antiperspirant active comprises a halohydrate or complex in which aluminium and zirconium are both present.

20. A composition according to claim 1 wherein the proportion of antiperspirant active is from 5 to 40% by weight of the composition.

21. An antiperspirant product comprising a dispensing container having an open end for extrusion of the contents of the container, means for urging the contents of the container towards the said open end, and a stick of composition according to claim 1 accommodated within the container.

22. A method of making a composition according to claim 1 comprising:
mixing the ingredients of the composition and, before, during or after mixing, heating the ingredients of the composition to a temperature at which continuous phase is a mobile liquid in which the fibre-forming structurant material (i) and the organic polymer thickener (ii) are dissolved in the water-immiscible liquid,
introducing the composition, at a temperature at which it is mobile, into containers,
causing or allowing cooling of the containers, until the temperature of the composition in the containers has fallen below 30° C.

23. A method according to claim 22 wherein the step of mixing and heating the ingredients comprises mixing the fibre-forming structurant and the polymeric thickener with the water immiscible liquid and, before, during or after mixing, heating them to a temperature at which continuous phase is a mobile liquid in which the fibre-forming structurant material and the organic polymer thickener are dissolved in the water-immiscible liquid, then adding a solution of antiperspirant active.

* * * * *